United States Patent
Shen et al.

(10) Patent No.: US 11,642,135 B2
(45) Date of Patent: May 9, 2023

(54) CIRCULAR STAPLING DEVICE WITH POSITION RIBS

(71) Applicant: Covidien LP, Mansfield, MA (US)

(72) Inventors: Dongming Shen, Shanghai (CN); Xiliang Zhang, Shanghai (CN); Syed Sarfraz Ahamed, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/554,352

(22) Filed: Dec. 17, 2021

(65) Prior Publication Data

US 2022/0104825 A1 Apr. 7, 2022

Related U.S. Application Data (63) Continuation of application No. 16/641,050, filed as application No. PCT/CN2017/100233 on Sep. 1, 2017, now Pat. No. 11,234,703.

(51) Int. Cl.
*A61B 17/064* (2006.01)
*A61B 17/115* (2006.01)
(Continued)

(52) U.S. Cl.
CPC . *A61B 17/1155* (2013.01); *A61B 2017/00477* (2013.01); *A61B 2017/07257* (2013.01);
(Continued)

(58) Field of Classification Search
CPC . A61B 17/068; A61B 17/115; A61B 17/1114; A61B 17/1115; A61B 2017/07257
See application file for complete search history.

(56) References Cited

U.S. PATENT DOCUMENTS 3,193,165 A  7/1965 Akhalaya et al.
3,388,847 A  6/1968 Kasulin et al.
(Continued)

FOREIGN PATENT DOCUMENTS

AU   2014206190 A1   8/2014
CA      908529 A     8/1972
(Continued)

OTHER PUBLICATIONS

Chinese Office Action dated Oct. 27, 2022, issued in corresponding Chinese Appln. No. 201780094391, 15 pages.
(Continued)

*Primary Examiner* — Eyamindae C Jallow
(74) *Attorney, Agent, or Firm* — Carter, DeLuca & Farrell LLP (57) ABSTRACT

A circular stapling device includes structure to position an anvil assembly in proper alignment with a cartridge assembly prior to firing of the stapling device. The stapling device includes an anvil assembly, a cartridge assembly including a staple cartridge and shell housing, and an anvil retainer that has a proximal portion including a longitudinal rib and a distal portion including at least one second longitudinal rib. The first longitudinal rib is received within a slot formed within the shell housing to prevent rotation of the anvil retainer in relation to the shell housing. The at least one second longitudinal rib is received within a longitudinal channel of the anvil assembly to prevent rotation of the anvil assembly in relation to the anvil retainer. The presently disclosed structure obviates the need for splines and the disadvantages associated with the use of splines.

20 Claims, 9 Drawing Sheets

(51) Int. Cl.
*A61B 17/00* (2006.01)
*A61B 17/072* (2006.01)

(52) U.S. Cl.
CPC .............. *A61B 2017/07271* (2013.01); *A61B 2017/07285* (2013.01)

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |

(56) References Cited

U.S. PATENT DOCUMENTS

| | | |
|---|---|---|
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |

(56) References Cited

U.S. PATENT DOCUMENTS

| | | |
|---|---|---|
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 3,002,795 A1 | 8/2011 | Beetel |
| 3,006,701 A1 | 8/2011 | Bilotti et al. |
| 3,006,889 A1 | 8/2011 | Adams et al. |
| 3,011,551 A1 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,540,132 B2 | 9/2013 | Marczyk et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,492,168 B2 | 11/2016 | Milliman |
| 11,234,703 B2 | 2/2022 | Shen et al. |
| 2003/0111507 A1 | 6/2003 | Nunez |
| 2004/0073090 A1 | 4/2004 | Butler et al. |
| 2005/0006433 A1 | 1/2005 | Milliman et al. |
| 2005/0023325 A1 | 2/2005 | Gresham et al. |
| 2005/0051597 A1 | 3/2005 | Toledano |
| 2005/0107813 A1 | 5/2005 | Gilete Garcia |
| 2005/0205640 A1 | 9/2005 | Milliman |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0075117 A1 | 4/2007 | Milliman et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0108741 A1 | 5/2010 | Hessler et al. |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |

(56) References Cited

U.S. PATENT DOCUMENTS

| | | |
|---|---|---|
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza |
| 2016/0157856 A1 | 6/2016 | Williams et al. |
| 2016/0174988 A1 | 6/2016 | D'Agostino et al. |
| 2016/0192934 A1 | 7/2016 | Williams et al. |
| 2016/0192938 A1 | 7/2016 | Sgroi, Jr. |
| 2016/0302792 A1 | 10/2016 | Motai |
| 2016/0310141 A1 | 10/2016 | Penna et al. |
| 2017/0245860 A1 | 8/2017 | Williams |
| 2018/0242974 A1 | 8/2018 | Guerrera et al. |

FOREIGN PATENT DOCUMENTS

| | | |
|---|---|---|
| CA | 2805365 A1 | 8/2013 |
| CN | 200957100 Y | 10/2007 |
| CN | 201768001 U | 3/2011 |
| CN | 201768002 U | 3/2011 |
| CN | 104287802 A | 1/2015 |
| CN | 107049402 A | 8/2017 |
| DE | 1057729 B | 5/1959 |
| DE | 3301713 A1 | 7/1984 |
| EP | 0152382 A2 | 8/1985 |
| EP | 03173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 2008107918 A1 | 9/2008 |
| WO | 2017053189 A1 | 3/2017 |

OTHER PUBLICATIONS

European Search Report dated Dec. 21, 2020, issued in corresponding EP Appln. No. 17923741, 10 pages.

International Search Report dated May 23, 2018, corresponding to counterpart International Application No. PCT/CN2017/100233; 3 pages.

CIRCULAR STAPLING DEVICE WITH POSITION RIBS

CROSS-REFERENCE TO RELATED APPLICATIONS

This application is a Continuation Application of U.S. patent application Ser. No. 16/641,050 filed on Feb. 21, 2020, which is a National Stage Entry of PCT/CN2017/100233 filed on Sep. 1, 2017, the entire contents of each of which are incorporated by reference herein.

BACKGROUND

1. Technical Description

The present disclosure is directed to circular stapling devices, and more particularly, to circular stapling devices including structure to properly align an anvil assembly with a staple cartridge of a shell assembly of the circular stapling device.

2. Background of Related Art

Circular stapling devices are utilized by clinicians to apply one or more surgical fasteners, e.g., staples or two-part fasteners, to body tissue for the purpose of joining segments of body tissue together and/or for the creation of an anastomosis. Circular stapling devices generally include a cartridge or shell assembly supporting a plurality of annular rows of staples, an anvil assembly operatively associated with the cartridge assembly and having annular arrays of staple receiving pockets for providing a surface against which the plurality of annular rows of staples can be formed, and an annular blade for cutting tissue.

During a typical tissue fastening procedure, the anvil assembly of the stapling device is positioned within one segment of body tissue and the shell assembly and a body portion of the stapling device supporting the shell assembly are positioned in an adjacent segment of body tissue. The anvil assembly is then attached to the body portion of the stapling device and the stapling device is actuated to approximate the anvil assembly with the cartridge assembly and clamp the body tissue segments together.

Typically, the anvil assembly includes an anvil shaft that includes splines that mate with splines formed within a shell housing of the shell assembly to align the staple forming pockets of the anvil assembly with staple receiving pockets of the staple cartridge of the shell assembly. Misalignment of the splines often results in misalignment of the staple forming pockets of the anvil assembly and the staple receiving pockets of the shell assembly such that malformation of the staples occurs during firing of the stapling device.

A continuing need exist for a circular stapling device including more reliable alignment structure for aligning the staple forming pockets of the anvil assembly with the staple receiving pockets of the shell assembly.

SUMMARY

In one aspect of the disclosure, a surgical stapling device includes a body portion and a tool assembly supported on a distal portion of the body portion. The tool assembly includes an anvil assembly and a cartridge assembly. The body portion includes an anvil retainer having a proximal portion and a distal portion. The proximal portion of the anvil retainer supports a first longitudinal rib and the distal portion of the anvil retainer supports a second longitudinal rib. The anvil assembly of the tool assembly has an anvil shaft and an anvil head supported on a distal portion of the anvil shaft. The anvil shaft has a plurality of resilient legs defining a bore. The resilient legs flex outwardly to facilitate passage of the anvil retainer into the bore. Adjacent resilient legs of the plurality of resilient legs define longitudinal channels. At least one of the longitudinal channels defined by the resilient legs receives the second longitudinal rib to prevent rotation of the anvil shaft in relation to the anvil retainer. The shell assembly is supported on a distal portion of the body portion and includes a shell housing having an inner housing portion defining a through bore. The anvil retainer extends through the through bore. A bushing is supported within the through bore of the inner housing portion of the shell housing. The bushing defines an internal slot that receives the first longitudinal rib to prevent rotation of the anvil retainer within the through bore of the bushing.

In another aspect of the disclosure, the surgical stapling device includes a body portion, an anvil assembly, and a cartridge assembly. The body portion includes an anvil retainer, having a proximal portion supporting a first longitudinal rib and a distal portion supporting at least one second longitudinal rib. The anvil assembly has an anvil shaft and an anvil head supported on a distal portion of the anvil shaft. The anvil shaft defines a longitudinal bore and at least one longitudinal channel. The longitudinal bore is dimensioned to receive the distal portion of the anvil retainer. The second longitudinal rib is received within the at least one longitudinal channel when the distal portion of the anvil retainer is received within the longitudinal bore to prevent rotation of the anvil assembly in relation to the anvil retainer. The shell assembly is supported on a distal portion of the body portion and includes a shell housing having an inner housing portion defining a through bore. The anvil retainer extends through the through bore. A bushing defining an internal slot is supported within the through bore of the inner housing portion of the shell housing. The internal slot receives the first longitudinal rib of the anvil retainer to prevent rotation of the anvil retainer within the through bore of the bushing.

In embodiments, the bushing includes an external slot and the inner housing portion includes an inner wall that defines the through bore. The inner wall of the inner housing portion supports a third longitudinal rib that is received within the external slot of the bushing to prevent rotation of the bushing within the through bore of the inner housing portion.

In some embodiments, the distal portion of the anvil retainer supports a plurality of second longitudinal ribs, wherein each of the plurality of second longitudinal ribs is received within a respective one of the longitudinal channels defined between the resilient legs of the anvil shaft.

In certain embodiments, the bushing is formed from a metal.

In embodiments, the stapling device includes a handle assembly and the body portion extends distally from the handle assembly.

In some embodiments, the shell assembly is releasably coupled to the body portion.

In certain embodiments, a distal portion of the bushing is formed with spaced rings that are positioned to engage the inner wall of the inner housing portion of the shell housing within the through bore to secure the bushing within the through bore.

In embodiments, the anvil head is pivotally supported on the anvil shaft.

BRIEF DESCRIPTION OF THE DRAWINGS

Various embodiments of the presently disclosed surgical stapling device are described herein below with reference to the drawings, wherein.

DETAILED DESCRIPTION OF EMBODIMENTS

The presently disclosed surgical stapling device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. In addition, the term clinician is used generally to refer to medical personnel including doctors, nurses, and support personnel.

The presently disclosed circular stapling device includes structure to position an anvil assembly in alignment with a cartridge assembly prior to firing of the stapling device. The stapling device includes an anvil assembly, a cartridge assembly including a staple cartridge and shell housing, and an anvil retainer that has a proximal portion including a longitudinal rib and a distal portion including at least one second longitudinal rib. The first longitudinal rib of the anvil retainer is received within a slot formed within the shell housing of the cartridge assembly to prevent rotation of the anvil retainer in relation to the shell housing. The at least one second longitudinal rib of the anvil retainer is received within a longitudinal channel of the anvil assembly to prevent rotation of the anvil assembly in relation to the anvil retainer. The presently disclosed structure obviates the need for splines and the disadvantages associated the use of splines.

Figure 1:
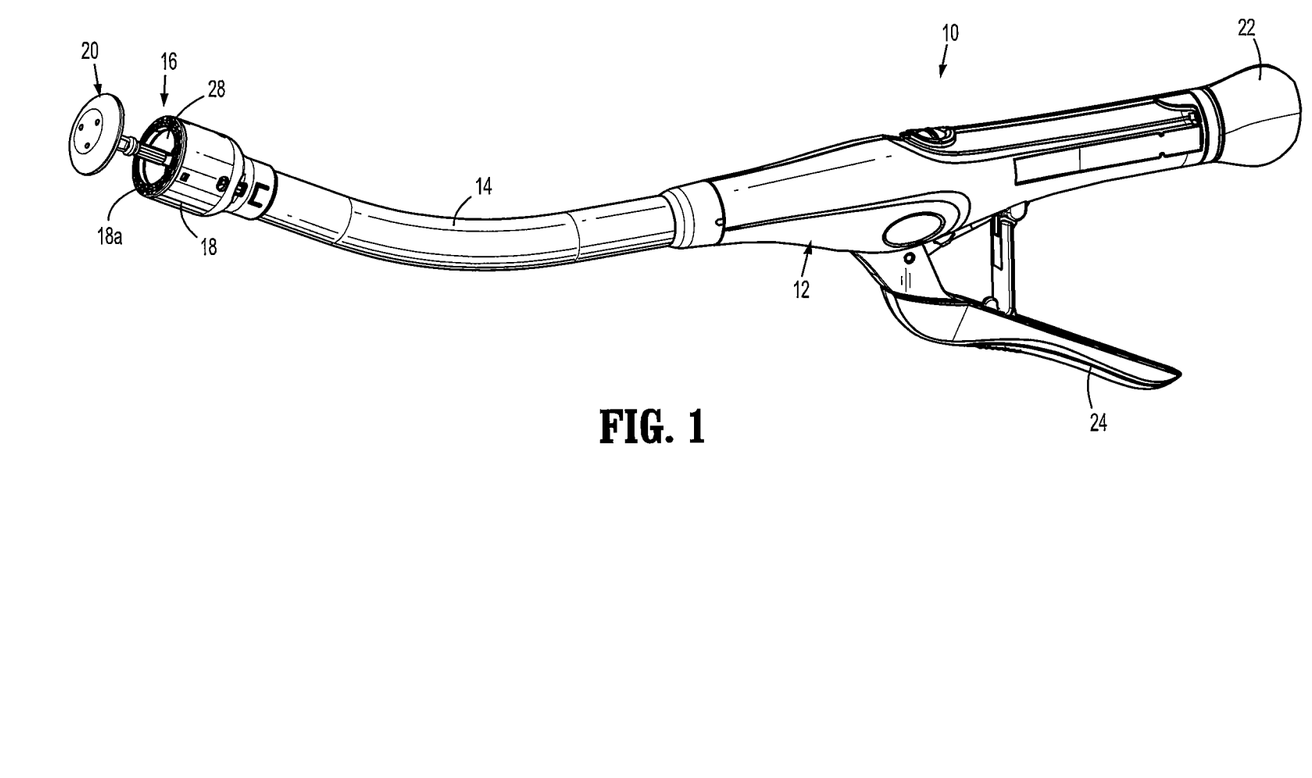
FIG. 1 is a side perspective view of an exemplary embodiment of the presently disclosed surgical stapling device with a tool assembly in an unclamped position.
Figure 2:
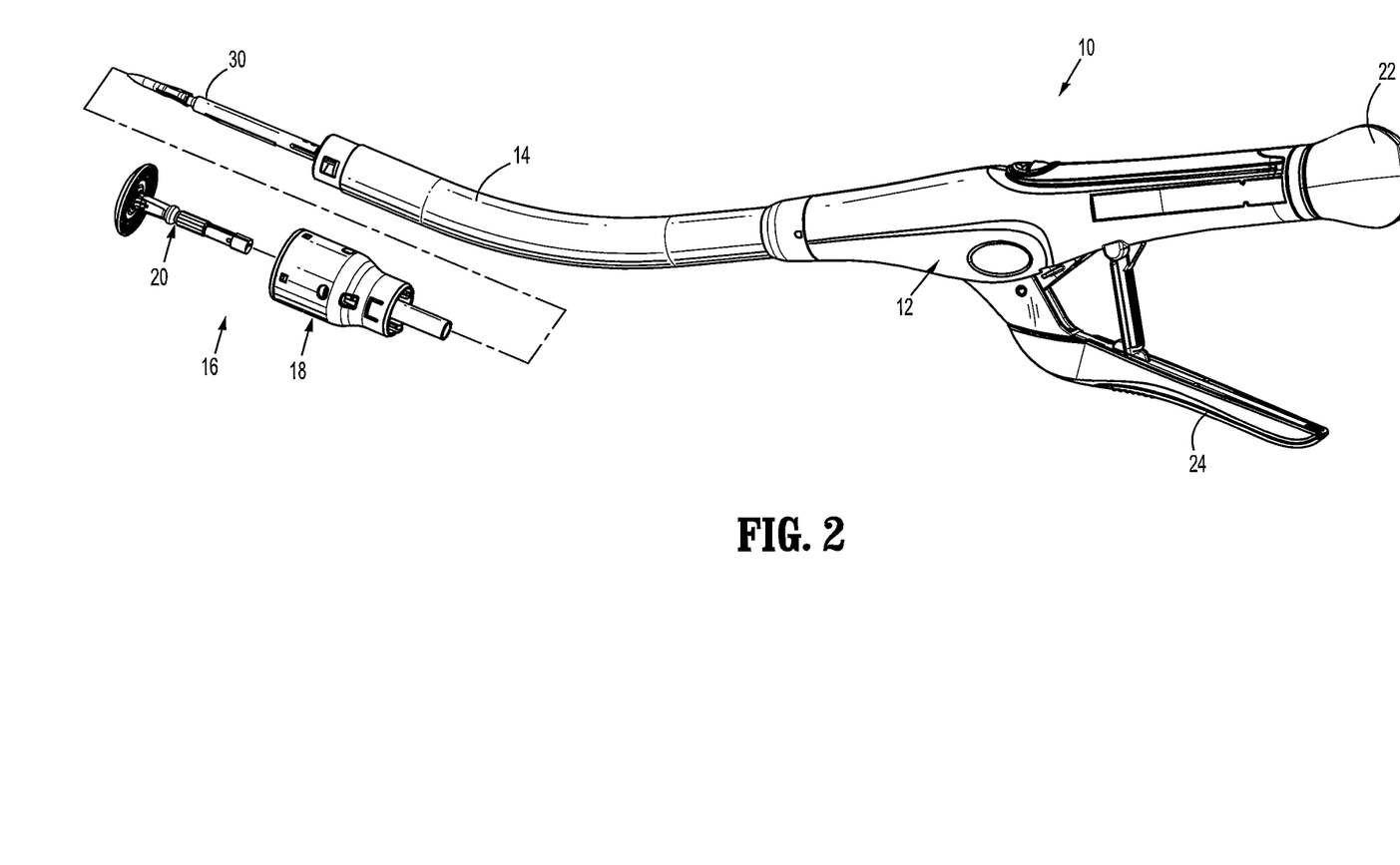
FIG. 2 is a side perspective view of the surgical stapling device shown in FIG. 1 with the tool assembly separated from the remaining portion of the stapling device.

Referring to FIGS. 1 and 2, the presently disclosed surgical stapling device shown generally as 10 includes a handle assembly 12, an elongated body portion 14 that extends distally from the handle assembly 12, and a tool assembly 16 that is supported on a distal portion of the elongated body portion 14. The tool assembly 16 includes an anvil assembly 20 and a cartridge or shell assembly 18 that supports a staple cartridge 18a. The handle assembly 12 includes an approximation knob 22 that operates an approximation mechanism (not shown) to move the anvil assembly 20 in relation to the cartridge assembly 18 between unclamped and clamped positions, and a firing trigger 24 that that operates a firing mechanism (not shown) to fire staples (not shown) from the staple cartridge 18a into tissue. For a detailed description of an exemplary circular stapling device including known approximation and firing mechanisms, see U.S. Pat. No. 7,857,187 ("the '187 Patent") which is incorporated herein by reference in its entirety.

Although the presently disclosed stapling device 10 is shown and described as being a manually powered device, it is envisioned that the stapling device 10 can be an electrically powered device such as described in U.S. Patent Publication No. 2012/0253329 which is incorporated herein by reference in its entirety.

The staple cartridge 18a of the shell assembly 18 has an annular configuration and the anvil assembly 20 includes an anvil 20a (FIG. 5) having an annular configuration. The anvil assembly 20 is supported on an anvil retainer 30 which forms part of the approximation mechanism (not shown) of the stapling device 10 and is configured to releasably engage the anvil assembly 20. The anvil retainer 30 includes a distal portion that extends from a distal end of the elongate body portion 14 of the stapling device 10 and through the shell assembly 18 to a position to engage the anvil assembly 20 and a proximal portion that is operatively connected to the approximation knob 22 such that rotation of the approximation knob 22 causes the anvil assembly 20 to move in relation to the staple cartridge 18a of the shell assembly 18 between an unclamped or spaced position and a clamped position. The shell assembly 18 includes an annular knife 28 (FIG. 1) that is movable from a retracted position to an advanced position within the shell assembly 18 during firing of the stapling device 10 to transect tissue clamped between the staple cartridge 18a and the anvil 20a.

The shell assembly 18 is releasably coupled to a distal portion of the elongated body 14 of the stapling device 10 to facilitate replacement of the shell assembly 18 after each use. Mechanisms for releasably coupling the shell assembly 18 to the elongate body portion 14 of the stapling device 10 are described in U.S. Patent Publication Nos. 2016/0310141, 2016/0192938, and 2016/0192934 which are incorporated herein in their entirety by reference.

Figure 3:
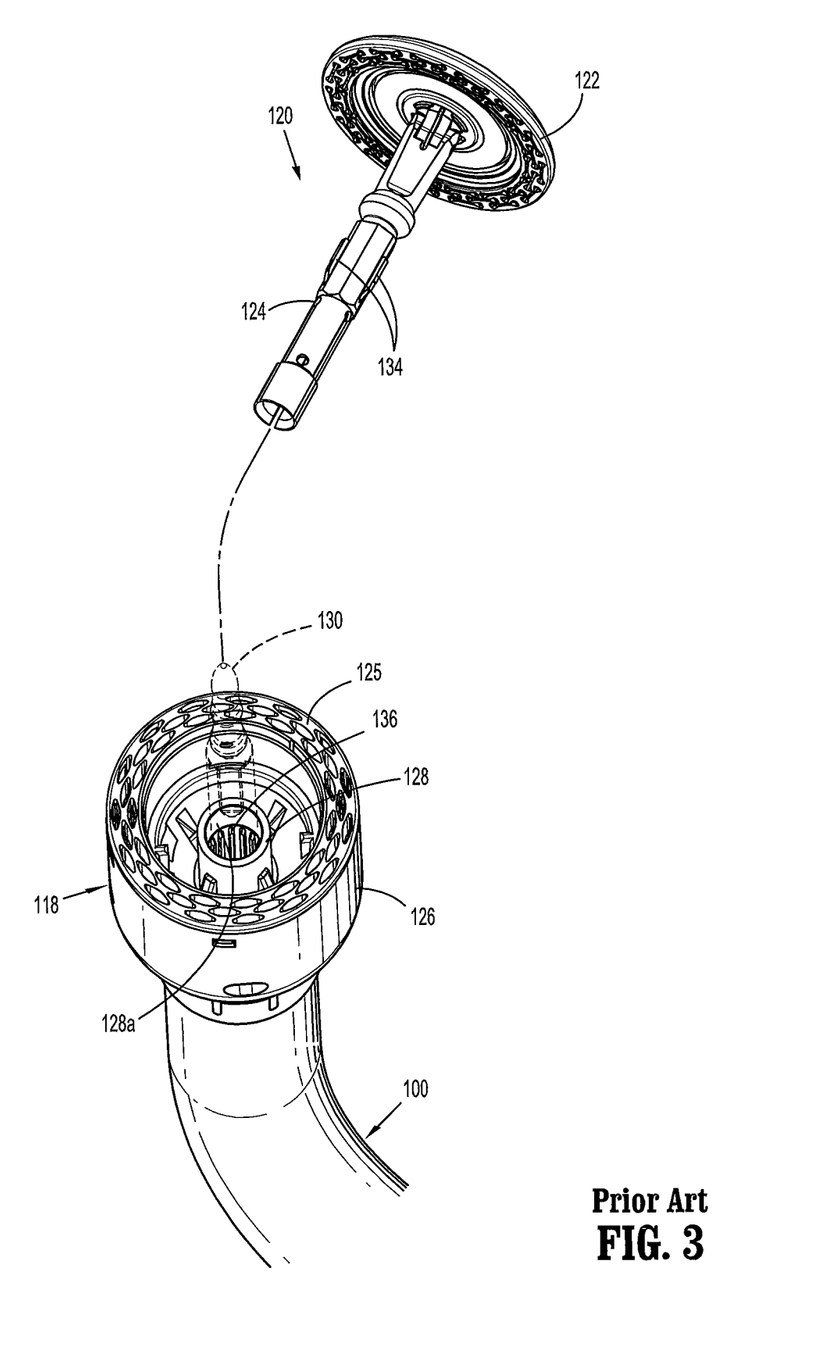
FIG. 3 is a perspective view from a distal end of a "Prior Art" surgical stapling device with an anvil assembly of a tool assembly of the surgical stapling device separated from the surgical stapling device.

Referring to FIG. 3, in "Prior Art" circular stapling devices 100, the anvil assembly 120 includes an anvil head 122 and an anvil shaft 124, and the shell assembly 118 includes a staple cartridge 125 and a shell housing 126 having an inner housing portion 128 that defines a through bore 128a. The anvil retainer 130 is received within the through bore 128a and is movable between retracted and advanced positions. When the anvil shaft 124 is coupled to the anvil retainer 130 and the anvil retainer 130 is retracted (via actuation of the approximation knob 22, FIG. 1), the anvil shaft 124 is drawn into the through bore 128a of the inner housing portion 128 of the shell housing 126. In order to properly align the anvil head 122 of the anvil assembly 120 with the staple cartridge 125 of the shell assembly 118, the anvil shaft 124 includes splines 134 that are received between splines 136 formed along an inner wall of the inner housing portion 128 of the shell housing 126. Receipt of the splines 134 of the anvil shaft 124 between the splines 136 of the shell housing 126 causes rotation of the anvil head 122 of the anvil assembly 120 in relation to the staple cartridge 125 of the shell assembly 118 to properly align the staple cartridge 125 with the anvil head 124 during approximation of the anvil assembly 120 and the shell assembly 118. As discussed briefly above, occasionally, the splines 134 and 136 crash or bind with each other and proper alignment between the anvil assembly 120 and the shell assembly 118 is not achieved. Such crashing and/or binding may result in improper staple formation or locking of the stapling device 100.

Figure 4:
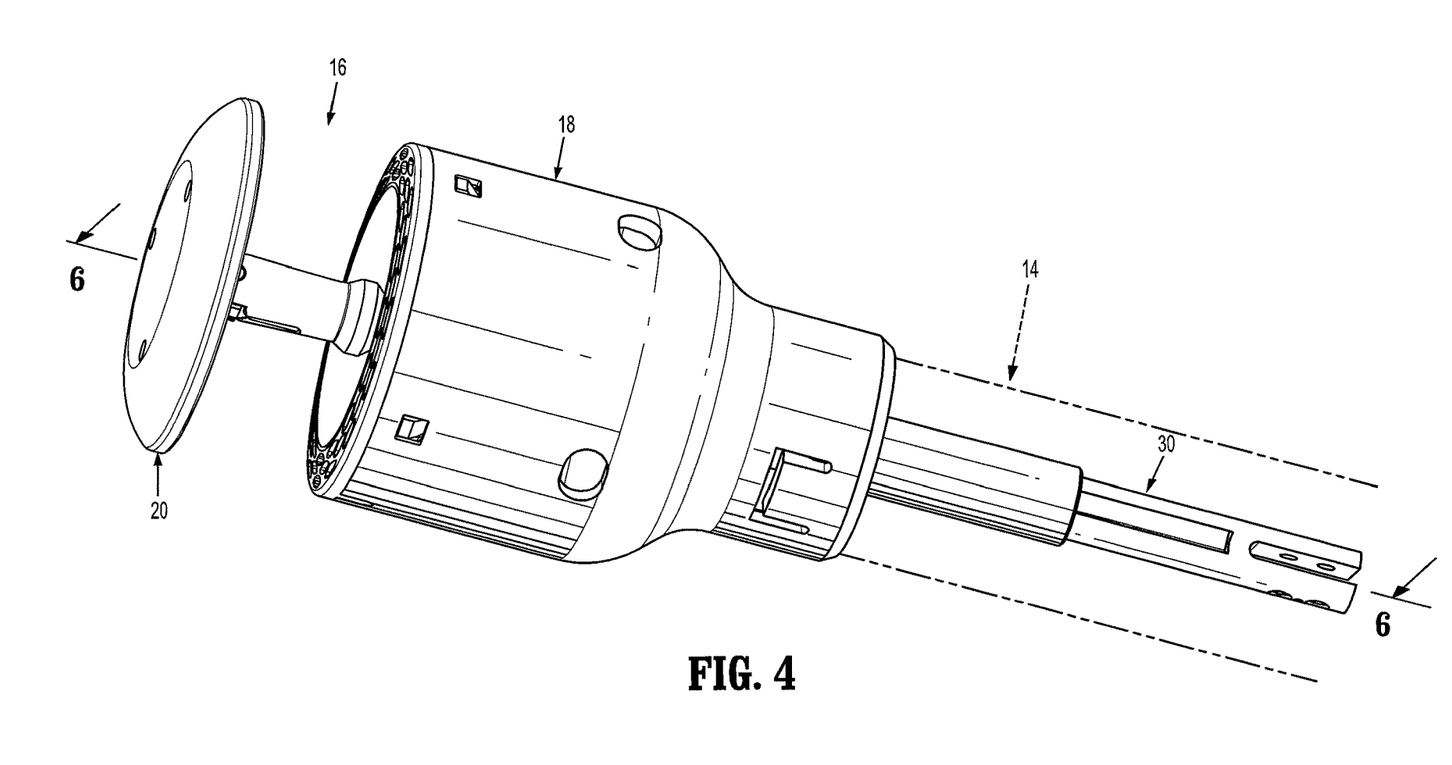
FIG. 4 is a side perspective view of the tool assembly and anvil retainer of the surgical stapling device shown in FIG. 1 with the tool assembly in an unclamped position and a body of the surgical stapling device shown in phantom.
Figure 5:
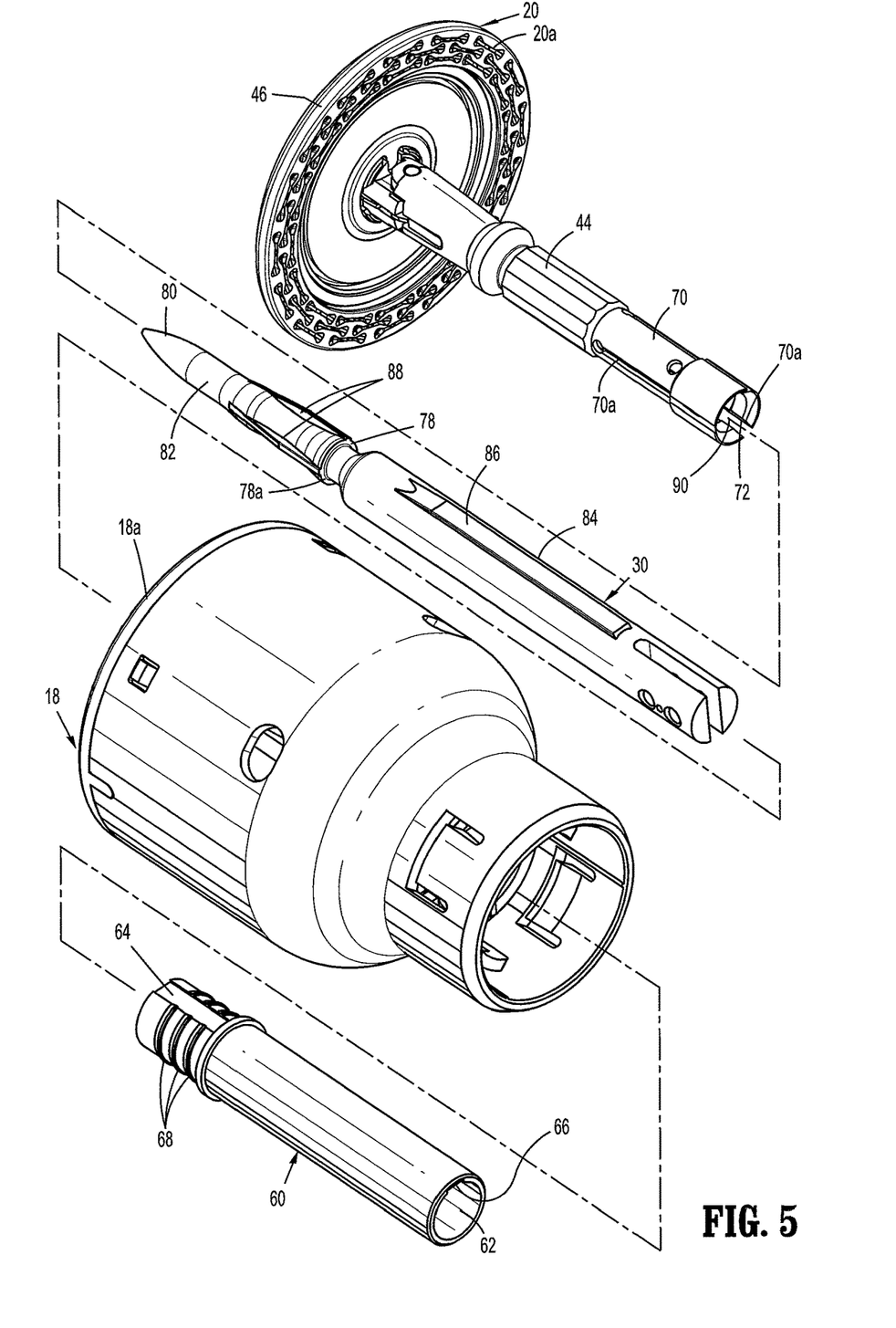
FIG. 5 is an exploded view of the tool assembly and anvil retainer shown in FIG. 4.
Figure 6:
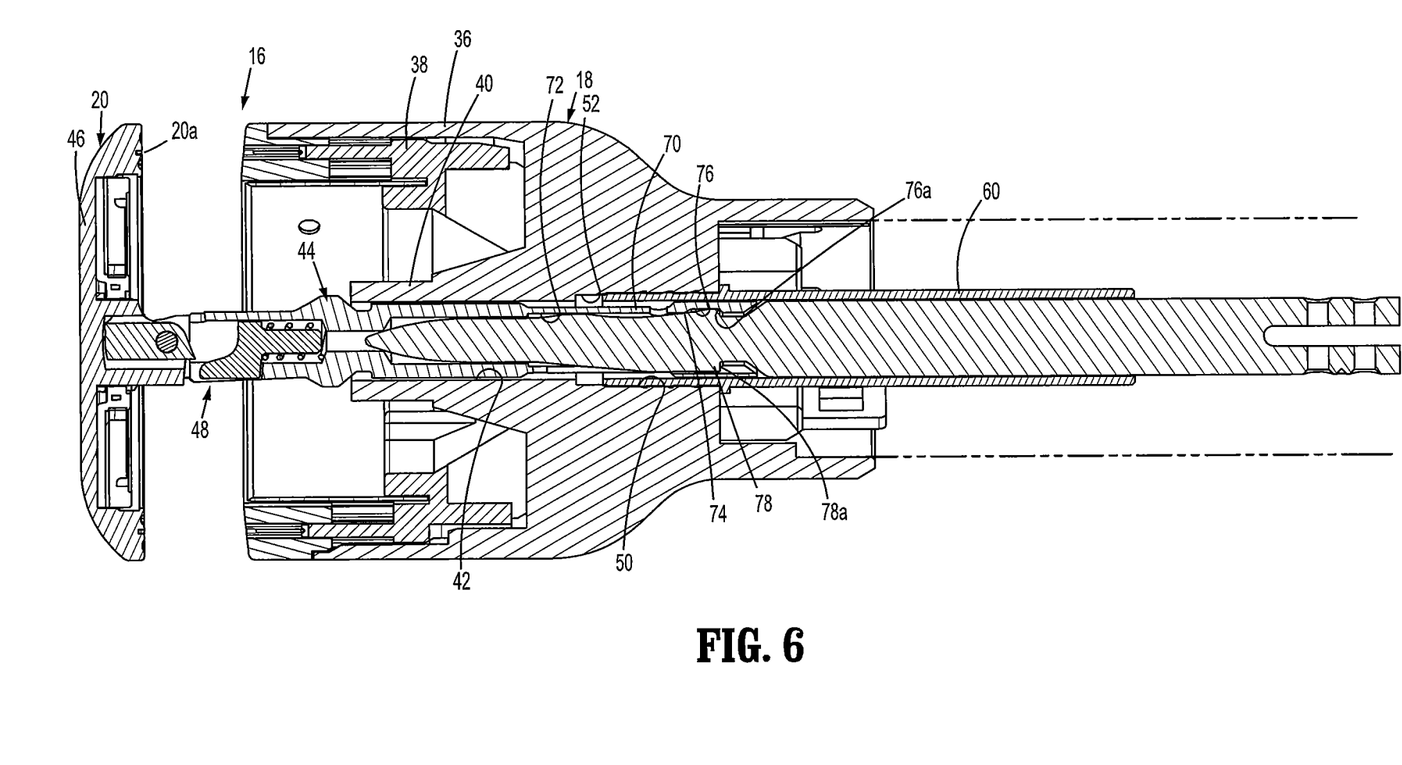
FIG. 6 is a cross-sectional view taken along section line 6-6 of FIG. 4.

Referring to FIGS. 4-6, as discussed above, the tool assembly 16 of the presently disclosed stapling device 10 (FIG. 1) includes a shell assembly 18 and an anvil assembly 20. The shell assembly 18 includes a shell housing 36 that supports the staple cartridge 18a and a pusher 38 (FIG. 6). The shell housing 36 includes an inner housing portion 40 (FIG. 6) that defines a through bore 42. The anvil assembly 20 includes an anvil shaft 44 and an anvil head 46 that is supported on a distal portion of the anvil shaft 44. In embodiments, the anvil head 46 is pivotally supported on the anvil shaft 44 and is urged to a tilted position by a biasing mechanism 48. The pivotal anvil head 46 and biasing mechanism 48 are known in the art and do not form part of the improvements disclosed in this application. U.S. Pat. Nos. 9,492,168 and 8,540,132 disclose exemplary pivotal anvil assemblies and biasing mechanisms and are incorporated herein by reference in their entirety.

In embodiments, the through bore 42 (FIG. 6) of the inner housing portion 40 of the shell housing 36 includes a proximal portion 50 having an increased diameter defining a step 52 between a distal portion of the through bore 42 and the proximal portion 50. The shell assembly 18 includes a substantially cylindrical bushing 60 that is received in the proximal portion 50 of the through bore 42. The bushing 60 defines a through bore 62 that is coaxial with the through bore 42 of the inner housing portion 40 of the shell housing 36. In embodiments, the bushing 60 defines an external slot 64 and an internal slot 66 which will be described in further detail below. In some embodiments, the distal portion of the bushing 60 is formed with spaced rings 68 that are dimensioned to engage an inner wall of the inner housing portion 40 of the shell housing 36 to secure the bushing 60 within the proximal portion 50 of the through bore 42. Alternately, other coupling methods or devices can be used to secure the bushing 60 within the inner housing portion 40 of the shell housing 36. In some embodiments, the bushing 60 is formed from a rigid, high strength material such as a metal, e.g., stainless steel. U.S. Pat. No. 9,492,168 ("the '168 Patent") which is incorporated herein by reference in its entirety.

The anvil assembly 20 includes the anvil shaft 44 and the anvil head 46 which is supported on the distal portion of the anvil shaft 44. In embodiments, the anvil shaft 44 includes a proximal portion having a plurality of resilient legs 70 that define a bore 72. The resilient legs 70 are spaced from each other to define longitudinal channels 70a between adjacent resilient legs 70. The bore 72 is dimensioned to receive the anvil retainer 30 to releasably secure the anvil shaft 44 to the anvil retainer 30. An inner wall 74 of each of the resilient legs 70 defines a recess 76 that defines a shoulder 76a. The recess 76 receives an abutment 78 formed on an outer surface of the anvil retainer 30 as is known in the art to secure a distal portion of the anvil retainer 30 within the bore 72 of the anvil shaft 44. See, e.g., the '168 Patent.

The anvil retainer 30 is secured to a distal portion of an approximation mechanism (not shown) and is advanced or retracted within the through bore 42 of the inner housing portion 40 of the shell housing 36 by rotating the approximation knob 22 (FIG. 1). In embodiments, the anvil retainer 30 includes a distal portion 80 that defines a trocar 82 having a tapered distal end and a larger diameter proximal portion 84 that is received within the through bore 42 of the inner housing portion 40 of the shell housing 36 and is secured to the approximation mechanism (not shown) of the surgical stapling device. In embodiments, the proximal portion 84 (FIG. 5) of the anvil retainer 30 supports a longitudinally extending first rib 86 and the distal portion 80 of the anvil retainer 30 includes at least one second rib 88. In embodiments, the at least one second rib 88 includes two ribs 88.

When the anvil assembly 20 is coupled to the anvil retainer 30, the distal portion of the anvil retainer 30 is inserted into an opening 90 (FIG. 5) defined at a proximal end of the resilient legs 70. When the abutment 78 formed on an outer surface of the anvil retainer 30 engages the resilient legs 70, the resilient legs 70 flex outwardly to facilitate further passage of the anvil retainer 30 into the anvil shaft 44. When the abutment 78 is moved into alignment with the recess 76 (FIG. 6), the resilient legs 70 flex inwardly such that the abutment 78 is received within the recess 76 and the anvil assembly 20 is releasably secured to the anvil retainer 30. The abutment 78 defines a shoulder 78a that engages the shoulder 76a defining the recess 76 to resist separation of the anvil assembly 20 from the anvil retainer 30.

Figure 7:
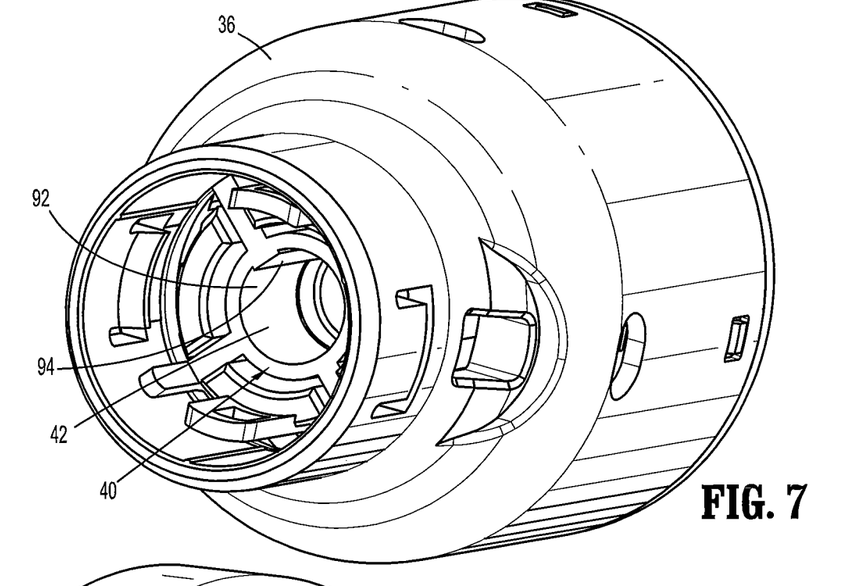
FIG. 7 is a side perspective view from a proximal end of the shell assembly of the tool assembly shown in FIG. 5 with a bearing member removed.
Figures 8, 9:
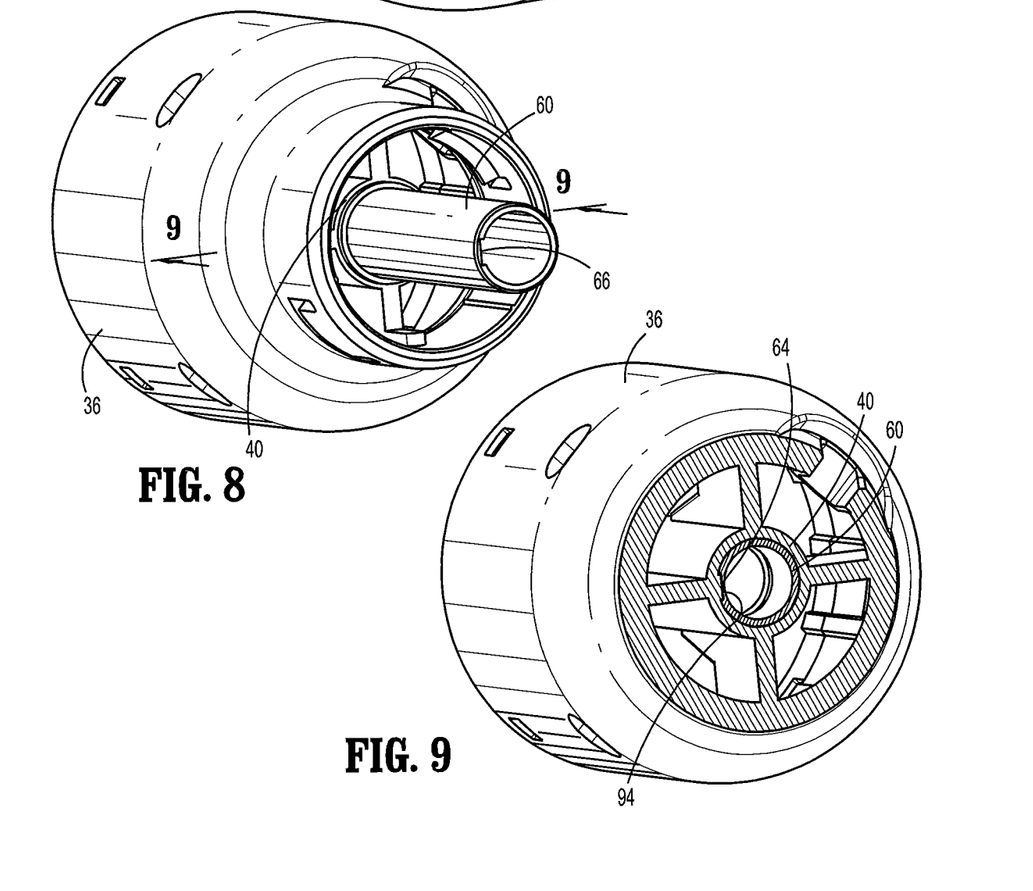
FIG. 8 is a side perspective view from the proximal end of the shell assembly of the tool assembly shown in FIG. 7 with the bearing member attached to the shell housing.
FIG. 9 is a cross-sectional view taken along section line 9-9 of FIG. 8.

Referring also to FIGS. 7-9, the inner housing portion 40 of the shell housing 36 includes an inner wall 92 that defines the through bore 42 of the inner housing portion 40. The inner wall 92 supports a longitudinal rib 94. When the bushing 60 is secured within the through bore 42 (FIG. 9) of the inner housing portion 40 of the shell housing 36, the longitudinal rib 94 is received within the external slot 64 defined in the distal portion of the bushing 60 (FIG. 9). Placement of the longitudinal rib 94 within the external slot 64 of the bushing 60 prevents the bushing 60 from rotating within the inner housing portion 40 of the shell housing 36.

Figures 10, 11, 12:
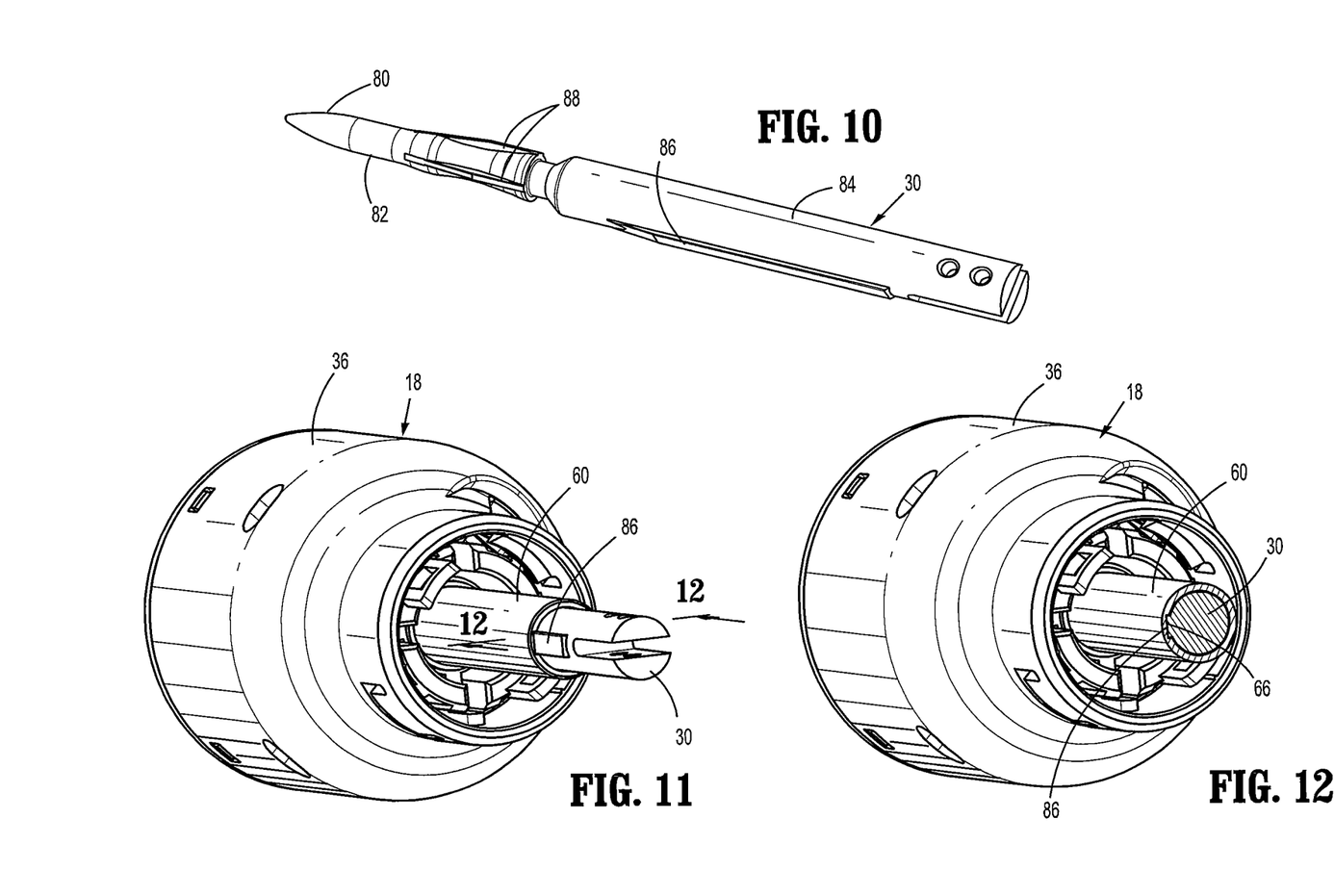
FIG. 10 is a side perspective view of the anvil retainer of the surgical stapling device shown in FIG. 2.
FIG. 11 is a side perspective view from the proximal end of the shell assembly of the tool assembly shown in FIG. 7 with the bearing member attached to the shell housing and the anvil assembly extending through the shell assembly in a retracted position.
FIG. 12 is a cross-sectional view taken along section line 12-12 of FIG. 11.

Referring to FIGS. 10-12, as discussed above, the through bore 62 of the bushing 60 defines an internal slot 66 (FIG. 12). When the anvil retainer 30 is received within the through bore 62 of the bushing 60, the longitudinally extending first rib 86 formed on the proximal portion 84 of the anvil retainer 30 is received within the internal slot 66 of the bushing 60. Placement of the longitudinally extending first rib 86 within the internal slot 66 of the bushing 60 prevents the anvil retainer 30 from rotating within the bushing 60.

Figures 13, 14:
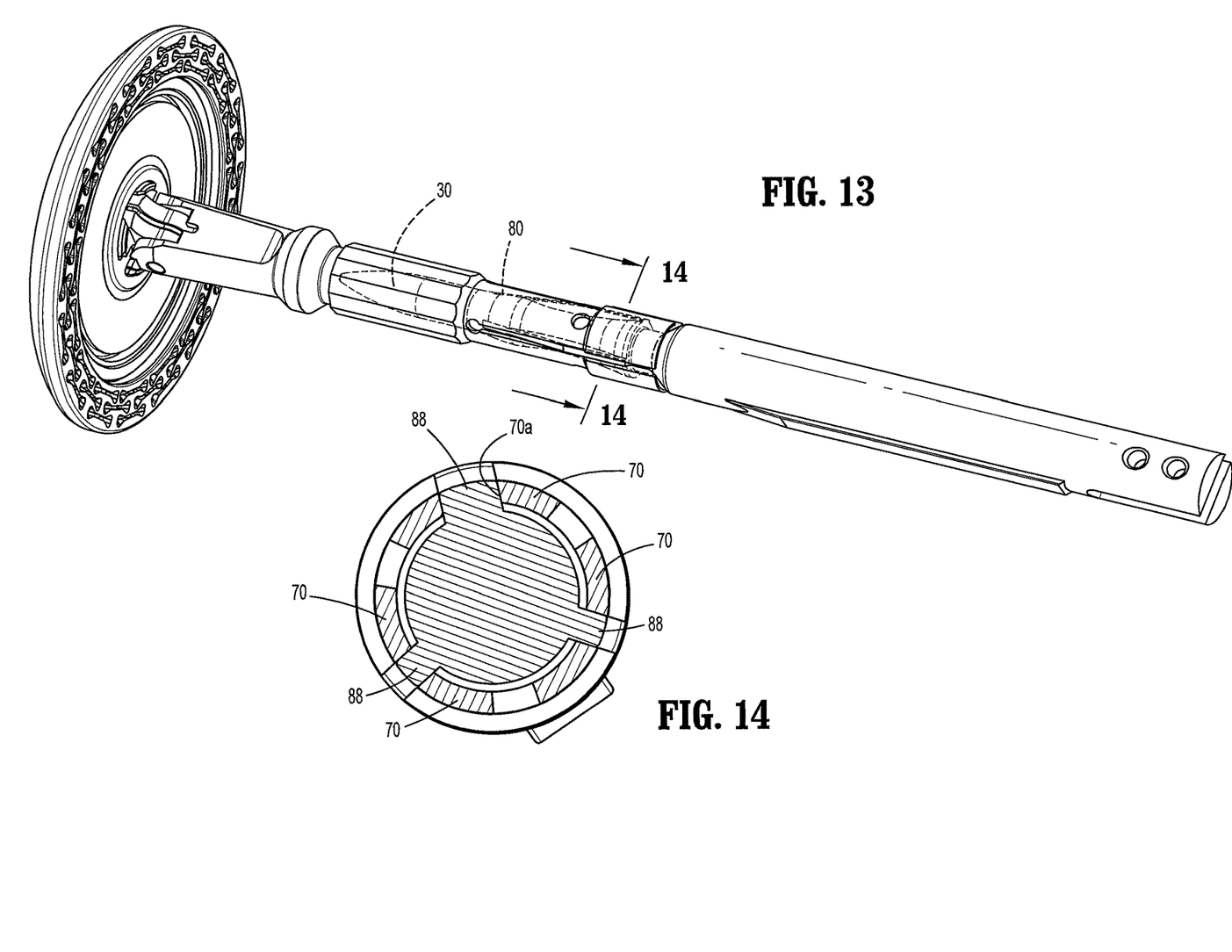
FIG. 13 is a side perspective view of the anvil assembly and anvil retainer of the surgical stapling device shown in FIG. 1.
FIG. 14 is a cross-sectional view taken along section line 14-14 of FIG. 13.

Referring to FIGS. 13 and 14, as the anvil retainer 30 is slid into the bore 72 (FIG. 5) of the anvil shaft 44, the longitudinally extending second ribs 88 formed on the distal portion 80 of the anvil retainer 30 are received in the respective longitudinal channels 70a defined between the resilient legs 70 of the anvil shaft 44. Receipt of the longitudinally extending second ribs 88 within the channels 70a defined between the resilient legs 70 prevents rotation of the anvil assembly 20 in relation to the anvil retainer 30.

In the presently disclosed stapling device 10, the anvil shaft 44 of the anvil assembly 20 does not include splines. Relative rotation between the anvil head 46 of the anvil assembly 20 and the staple cartridge 18a of the shell assembly 18 is prevented by including first and second longitudinal ribs 86, 88 on the anvil retainer 30 to prevent rotation of the anvil retainer 30 in relation to the shell housing 36 and to prevent rotation of the anvil assembly 20 in relation to the anvil retainer 30.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
    a body portion including an anvil retainer, the anvil retainer having a proximal portion and a distal portion, the distal portion defining a trocar, the proximal portion supporting a first longitudinal rib;
    a shell assembly supported on a distal portion of the body portion, the shell assembly including a shell housing having an inner housing portion defining a through bore, the anvil retainer extending through the through bore; and
    a bushing supported within the through bore of the inner housing portion of the shell housing, the bushing defining an internal slot, wherein the internal slot receives the first longitudinal rib to prevent rotation of the anvil retainer within the through bore of the bushing.

2. The surgical stapling device of claim 1, wherein the distal portion of the anvil retainer supports at least one second longitudinal rib, wherein the at least one second longitudinal rib is received within a respective one of longitudinal channels defined between legs of an anvil shaft of an anvil assembly.

3. The surgical stapling device of claim 2, wherein the bushing includes an external slot, and the inner housing portion of the shell assembly includes an inner wall that defines the through bore, the inner wall of the inner housing portion supporting a third longitudinal rib, the third longitudinal rib being received within the external slot of the bushing to prevent rotation of the bushing within the through bore of the inner housing portion.

4. The surgical stapling device of claim 3, wherein the first longitudinal rib is offset from the second longitudinal rib.

5. The surgical stapling device of claim 1, wherein the bushing is formed from a metal.

6. The surgical stapling device of claim 1, further including a handle assembly, the body portion extending distally from the handle assembly.

7. The surgical stapling device of claim 1, wherein the shell assembly is releasably coupled to the body portion.

8. The surgical stapling device of claim 1, wherein a distal portion of the bushing is formed with spaced outer rings, the spaced outer rings being positioned to engage the inner wall of the inner housing portion of the shell housing within the through bore to secure the bushing within the through bore.

9. A surgical stapling device comprising:
    a body portion including an anvil retainer, the anvil retainer having a proximal portion supporting a first longitudinal rib and a distal portion supporting at least one second longitudinal rib, the distal portion defining a trocar;
    a shell assembly supported on a distal portion of the body portion, the shell assembly including a shell housing having an inner housing portion defining a through bore, wherein the anvil retainer extends through the through bore; and
    a bushing supported within the through bore of the inner housing portion of the shell housing, the bushing defining an internal slot, the internal slot receiving the first longitudinal rib of the anvil retainer to prevent rotation of the anvil retainer within the through bore of the bushing.

10. The surgical stapling device of claim 9, wherein the at least one second longitudinal rib is positioned and configured to engage an anvil shaft of an anvil assembly to prevent rotation of the anvil shaft relative to the anvil retainer.

11. The surgical stapling device of claim 10, wherein the distal portion of the anvil retainer supports a plurality of second longitudinal ribs, each of the plurality of second longitudinal ribs.

12. The surgical stapling device of claim 9, wherein the bushing includes an external slot and the inner housing portion of the shell assembly includes an inner wall that defines the through bore, the inner wall of the inner housing portion including a third longitudinal rib, the third longitudinal rib being received within the external slot of the bushing to prevent rotation of the bushing within the through bore of the inner housing portion.

13. The surgical stapling device of claim 12, wherein the bushing has a distal portion formed with spaced rings, the spaced rings being positioned to engage the inner wall of the inner housing portion of the shell assembly within the through bore to secure the bushing within the through bore.

14. The surgical stapling device of claim 9, wherein the bushing is formed from a metal.

15. The surgical stapling device of claim 9, further including a handle assembly, the body portion extending distally from the handle assembly.

16. The surgical stapling device of claim 9, wherein the shell assembly is releasably coupled to the body portion.

17. A surgical stapling device comprising: a body portion including an anvil retainer, the anvil retainer having a proximal portion supporting a first longitudinal rib and a distal portion supporting at least one second longitudinal rib, the distal portion defining a trocar.

18. The surgical stapling device of claim 17, further including a shell assembly supported on a distal portion of the body portion, the shell assembly including a shell housing having an inner housing portion defining a through bore, wherein the anvil retainer extends through the through bore.

19. The surgical stapling device of claim 18, further including a bushing supported within the through bore of the inner housing portion of the shell housing, the bushing defining an internal slot, wherein the internal slot receives the first longitudinal rib of the anvil retainer to prevent rotation of the anvil retainer within the through bore of the bushing.

20. The surgical stapling device of claim 17, wherein the at least one second longitudinal rib is configured to engage an anvil shaft of an anvil assembly to prevent rotation of the anvil shaft relative to the anvil retainer.

* * * * *